United States Patent
van Lammeren et al.

(10) Patent No.: US 9,891,254 B2
(45) Date of Patent: Feb. 13, 2018

(54) CAPACITIVE SENSING SYSTEM AND METHOD

(71) Applicant: NXP B.V., Eindhoven (NL)

(72) Inventors: Johannes van Lammeren, Beuningen (NL); Frans Widdershoven, Eindhoven (NL)

(73) Assignee: NXP B.V., Eindhoven (NL)

(*) Notice: Subject to any disclaimer, the term of this patent is extended or adjusted under 35 U.S.C. 154(b) by 114 days.

(21) Appl. No.: 14/526,913

(22) Filed: Oct. 29, 2014

(65) Prior Publication Data
US 2015/0130482 A1 May 14, 2015

(30) Foreign Application Priority Data

Nov. 14, 2013 (EP) .................................... 13192869

(51) Int. Cl.
| | |
|---|---|
| *G01R 27/26* | (2006.01) |
| *G01R 23/02* | (2006.01) |
| *G01R 1/30* | (2006.01) |
| *G01N 27/22* | (2006.01) |

(52) U.S. Cl.
CPC ....... *G01R 27/2605* (2013.01); *G01N 27/221* (2013.01); *G01R 1/30* (2013.01); *G01R 23/02* (2013.01); *G01N 2027/222* (2013.01)

(58) Field of Classification Search
CPC ........ G01N 27/221; G01R 1/30; G01R 23/02; G01R 27/2605
USPC ......................................................... 324/682
See application file for complete search history.

(56) References Cited

U.S. PATENT DOCUMENTS

| | | | |
|---|---|---|---|
| 5,270,633 A | 12/1993 | Sano et al. | |
| 5,973,981 A * | 10/1999 | Lee .................. | G11C 29/36 365/102 |
| 7,023,221 B1 * | 4/2006 | Lin .................. | G01D 5/24 324/662 |
| 8,098,240 B2 * | 1/2012 | Zielinski et al. ... | A63F 3/00643 345/174 |
| 2005/0146383 A1 * | 7/2005 | Moore et al. ........ | G06K 9/0002 331/57 |
| 2010/0295580 A1 * | 11/2010 | Liu .................. | H03M 1/60 327/77 |
| 2011/0269648 A1 | 11/2011 | Schwartz | |

FOREIGN PATENT DOCUMENTS

| | | |
|---|---|---|
| CN | 20242115 U | 9/2012 |
| EP | 1 452 867 A1 | 9/2004 |
| EP | 2 242 541 A1 | 7/2011 |

(Continued)

OTHER PUBLICATIONS

Efstathios D. Kyriakis-Bitzaros, "A Reconfigurable Multichannel Capacitive Sensor Array Interface", Sep. 2011, IEEE Transactions on Instrumentation and Measurement, vol. 60, No. 9, pp. 3214-3221.*

(Continued)

*Primary Examiner* — Son Le
*Assistant Examiner* — Akm Zakaria

(57) ABSTRACT

The invention provides a capacitive sensor circuit in which a capacitance to be sensed is selectively coupled into a ring oscillator circuit. The ring oscillator frequency is measured with the capacitance coupled and not coupled, and a capacitance is derived from the change in ring oscillator frequency.

14 Claims, 3 Drawing Sheets

(56) References Cited

FOREIGN PATENT DOCUMENTS

| WO | 03/069360 A1 | 8/2003 |
| WO | 2009/047703 A1 | 4/2009 |

OTHER PUBLICATIONS

Kyriakis-Bitzaros, Efstathios D., et al; "A Reconfigurable Multi-channel Capacitive Sensor Array Interface"; IEEE Transactions on Instrumentation and Measurements, vol. 60, No. 9; (8 pages) (Sep. 2011).

Zampetti, E., et al; "Flexible sensorial system based on capacitive chemical sensors integrated with readout circuits fully fabricated on ultra thin substrate"; Sensors and Actuators B 155; pp. 768-774 (2011).

Extended European Search Report for application 13192869.9 (dated Jul. 14, 2014).

\* cited by examiner

CAPACITIVE SENSING SYSTEM AND METHOD

CROSS-REFERENCE TO RELATED APPLICATIONS

This application claims the priority under 35 U.S.C. § 119 of European patent application no. 13192869.9, filed on Nov. 14, 2013, the contents of which are incorporated by reference herein.

FIELD OF THE INVENTION

This invention relates to a capacitive sensing system.

BACKGROUND OF THE INVENTION

The invention is of particular interest for pixellated capacitive sensing systems, which can be used to determine material properties.

This type of pixellated capacitive sensing system can for example consist of an electronic circuit capable of measuring extremely small capacitances, originating from a chemical substance which changes its dielectric constant under the influence of a material to be detected. To obtain as much information as possible the sensor is not one big component, but an array of "pixels" (like image sensors). The pixellation enables measurement of gradients, and detection of material boundaries and imperfections.

An example is measuring the amount of $CO_2$ in ambient air.

There are a number of different ways to measure capacitance. The capacitor under measurement can be driven with either a voltage or a current excitation signal. The output signal can be the current or voltage that flows as a result of the excitation, but it can also be a ratio or difference signal.

Examples of possible combinations of excitation signal and readout signal are:

(i) AC voltage drive, measurement of the AC current through capacitor;
(ii) AC current drive, measurement of the AC voltage across capacitor;
(iii) AC voltage drive, measurement of the DC current through switched capacitor;
(iv) AC current drive, measurement of the DC voltage across switched capacitor;
(v) AC voltage drive, measurement of the capacitance ratio using a bridge circuit;
(vi) AC current drive, measurement of the capacitance ratio using a dual slope converter;
(vii) AC voltage drive, measurement of the capacitance difference using a switched difference integrator;
(viii) AC current drive, measurement of the capacitance difference;
(ix) Determination of an oscillation frequency dependent on the capacitance, for example using an oscillator.

Known pixelated sensors (also known as array impedance sensors) generally use AC voltage driving with measurement of the AC current through a capacitor (method (i) above). The change of the capacitance is interpreted to determine substance properties. A known biosensor makes use of AC voltage drive with measurement of the DC current through a switched capacitor (method (iii) above).

There is a need for a measurement approach which is accurate and can be implemented with simple circuitry.

SUMMARY OF THE INVENTION

The invention is defined by the claims.

According to an aspect of the invention, there is provided a capacitor sensor, comprising:
an array of sensor circuits arranged in rows and columns, each sensor circuit comprising:
a ring oscillator having a forward path and a feedback path;
an input for connection to a terminal of a capacitance to be measured; and
a switch between the input and a node on the forward path or
feedback path of the ring oscillator;
wherein the sensor further comprises:
a measuring circuit for measuring the ring oscillator frequency of each sensor circuit with the switch open and with the switch closed, and for deriving a capacitance from a change in ring oscillator frequency, wherein the measuring circuit comprises a row selector, a measuring unit for each column and a reference oscillator.

This capacitive sensor circuit makes use of an array of ring oscillators, each of which is used as part of a capacitor sensor circuit. This type of oscillator is slightly more noisy and power hungry than an LC oscillator, but it is much more compact, and so enables integration of many sensor circuits. In an IC sensor, many hundreds or even thousands of pixels may be desired, for which LC oscillators are usually too large.

The invention is based on the recognition that the most sensitive way to measure capacitance is to make the capacitance to be measured part of the frequency-determining components of an oscillator. This is due to the fact that time is the quantity that can be measured most accurately. Other methods often use time as the actual measurement quantity, but need a conversion to turn e.g. voltage information into time information.

The switch can be between the input and a node on the forward path of the ring oscillator. The capacitance thus changes the characteristics of the forward path of the ring oscillator, and thereby influences the resonant frequency.

The circuit can further comprise a gate at the input to the forward path which controls connection of the feedback path.

The forward path can then comprise the gate which is a NAND gate, and exactly two inverters in series.

The node to which the capacitance to be measured is coupled can then be at the input of the first inverter.

The ring oscillator can comprise an inverter after the forward and feedback paths, for isolating the output from the ring oscillator loop.

The invention enables a pixellated capacitor sensor to be formed. Each measuring unit preferably comprises a counter arrangement clocked by the ring oscillator output, for counting ring oscillator cycles during a measurement window with the switch open and with the switch closed. This provides a direct measurement of time, which enables an accurate measurement of the ring oscillator frequency.

The counter arrangement preferably comprises first and second counters, and wherein each counter has an output latch. This latch stores the measured count, for subsequent analysis to derive the measured capacitance.

The circuit can comprise a divider for dividing the reference oscillator output to derive an enable signal, wherein the controller derives the control signal for the switch from the enable signal. In this way, the switch is controlled for a duration which is a number of reference clock cycles.

The sensor circuit can be used for gas sensing, humidity sensing, electronic noses and tongues, biosensing, DNA sequencing, imaging of living cells, detecting particles in air or in fluids, detecting microscopic changes in layers deposited on an array of sense capacitors, etc.

The invention also provides a capacitive sensing method, comprising:

for each sensor circuit of an array of sensor circuits:
selectively coupling a terminal of a capacitance to be measured to a node in the forward path or feedback path of a respective sensor circuit ring oscillator;
measuring the ring oscillator frequency with the terminal coupled and with the terminal decoupled; and
deriving a capacitance from the change in ring oscillator frequency.

BRIEF DESCRIPTION OF THE DRAWINGS

Examples of the invention will now be described in detail with reference to the accompanying drawings, in which.

DETAILED DESCRIPTION

The invention provides a capacitive sensor circuit in which a capacitance to be sensed is selectively coupled into a ring oscillator circuit. The ring oscillator frequency is measured with the capacitance coupled and not coupled, and a capacitance is derived from the change in ring oscillator frequency.

The invention is based on the recognition that the most sensitive way to measure capacitance is to make the capacitance to be measured part of the frequency-determining components of an oscillator. This is due to the fact that time is the quantity that can be measured most accurately. Other methods often use time as the actual measurement quantity, but need a conversion to turn e.g. voltage information into time information.

As each conversion adds noise and distortion, information is lost if there is not a direct frequency or time measurement.

Figure 1:
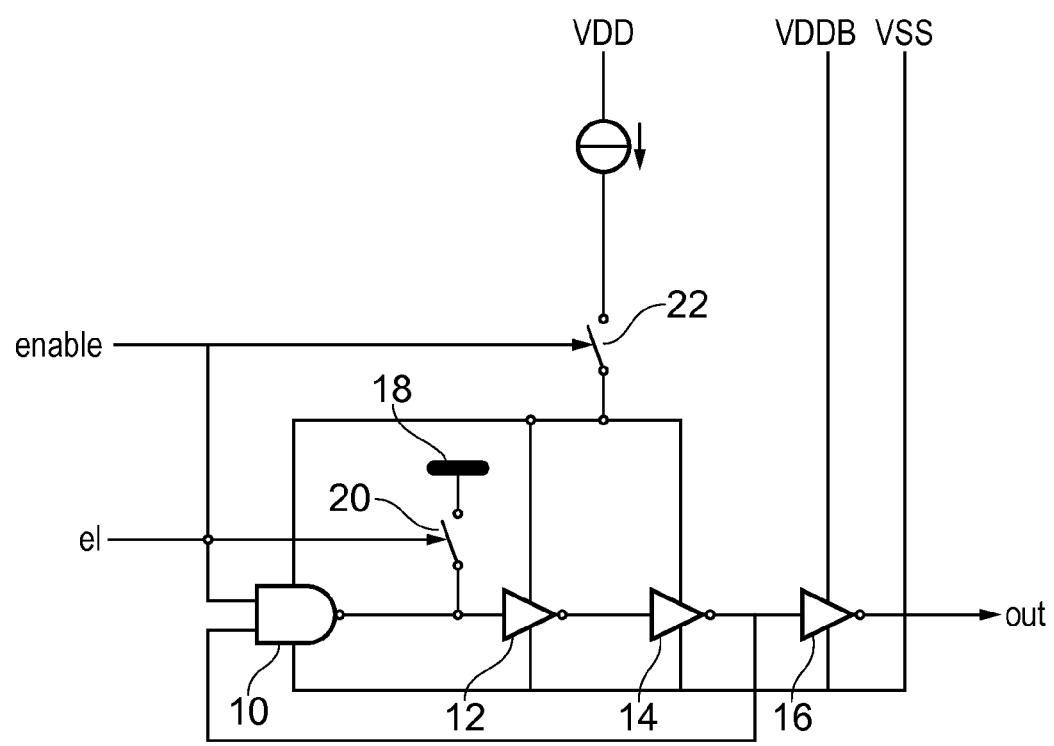
FIG. 1 shows an oscillator circuit forming part of an individual capacitance measurement circuit of the invention.

FIG. 1 shows an example of a ring oscillator for use in a pixelated sensor of the invention.

The oscillator loop consists of a NAND gate 10 and two inverters 12,14. The two inverters and the NAND gate define the forward path of the oscillator loop, and there is a feedback path from the output to the input. The loop thus has three inversions; one carried out by the NAND gate and two carried out by the inverters.

The NAND gate 10 allows the oscillator to be enabled at the desired time and also provides a predictable start up behaviour. The feedback path connects to one terminal of the NAND gate, and an enable signal "enable" connects to the other terminal of the NAND gate. If the enable signal "enable" is low, the NAND gate output is constant and the oscillation stops. When the enable signal is high, the oscillator loop essentially comprises three inverter stages.

By implementing one inverter as a logic gate, this circuit has some advantages over a traditional three-inverter ring oscillator. A ring oscillator with three inverters can only be stopped by switching off its supply. To start up such a ring oscillator needs some noise, making the start-up behaviour less predictable.

A third inverter 16 is provided at the output of the ring oscillator (after the feedback path). This is a buffer to isolate the output line from the oscillation loop and to provide the power to drive this output line. The buffer is designed to have a high output impedance when the associated oscillator is not active, so as not to load an active oscillator (which in an array configuration may be coupled to the same output line).

The electrode input signal "el" controls a switch 20 that switches a capacitor electrode 18 into the loop. With the electrode in the loop, the oscillation frequency will be lower than without. How much lower is determined by the properties of the material on top of the electrode.

The relative change in oscillation frequency is approximately $C\_el/(4*C\_inv)$, where $C\_el$ is the capacitance of the electrode, $C\_inv$ is the input capacitance of an inverter Thus, the capacitance can be determined from the known inverter input capacitance, and the measured oscillation frequencies with the switch open and closed. Of course, more complicated relationships between frequency and the capacitance being sensed can be derived, which will depend on the particular way the circuit is implemented. Essentially, by switching the capacitance to be sensed into the circuit a change in frequency results. This change function needs to be modelled either by an equation as above, or even by calibration and a look up table. In either case, a frequency measurement then enables the capacitance to be derived. The derived capacitance is then used further to derive properties which influence the capacitance, such as the concentration of a material being sensed.

In the example, shown, the "enable" signal is used to drive one input of the NAND gate 10 as explained above, and is also used to control a power switch 22 which controls the supply of power to the oscillator loop inverters and NAND gate. In this way, power consumption is reduced when the sensor is not active. However, this power switch is not necessary in all implementations. Depending on the oscillation frequency, the supply current can be very small. The power switch 22 helps to reduce the leakage current when the oscillator is not active. As the oscillator consists of few components the leakage current reduction will not be very large, so if possible the power switch can be omitted to keep the oscillator size minimal.

The power switch 22 and the electrode switch 20 can be made with a pass gate. If the supply current is very small, the voltage across the NAND gate and inverters is much lower than the supply voltage VDD, so that they can be made with a single NMOS or PMOS transistor.

A measuring circuit is used to measure the ring oscillator frequency with the electrode switch 20 open and with the electrode switch 20 closed, so that the capacitance can be derived from the change in ring oscillator frequency.

Figure 2:
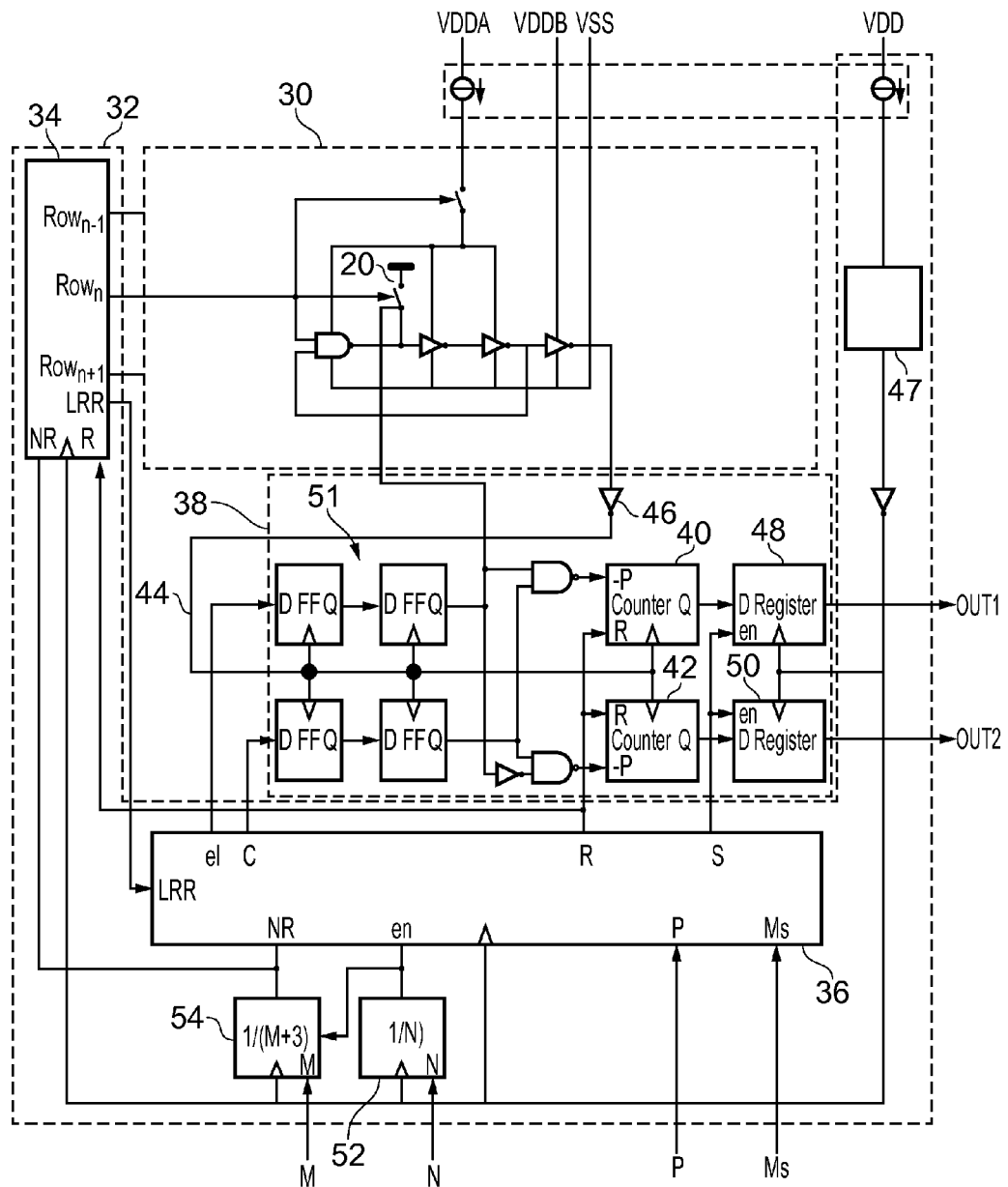
FIG. 2 shows an example of sensing circuit of the invention.

FIG. 2 shows the measuring circuit.

The sensor comprises an array of rows and columns of sensor circuits, each one in the form of the circuit of FIG. 1. Each sensor circuit can be considered to be a sensor pixel or a sensor cell.

FIG. 2 shows one such sensor circuit 30. The signal lines entering the sensor circuit 30 from top and bottom are connected to each sensor circuit in a column. The signal lines entering the sensor circuit 30 from the left is connected to each sensor circuit in a row.

The measuring circuit has a first set 32 of components which control the full array of sensor circuits. This first set comprises a row selector 34 which provides the enable signal to the rows in turn. This signal is shown as "$Row_{n-1}$", "$Row_n$" and "$Row_{n+1}$", and the sensor circuit shown is in $Row_n$.

A controller 36 generates the signal NR (Next Row) for controlling the row selector 34. The row selector generates a signal LRR (Last Row Ready) for feedback to the controller 36.

The row selector also receives a reset signal R also generated by the controller 36.

A second set 38 of components is provided for each column of sensor circuits.

It comprises a counter arrangement, having a first counter 40 for counting when the electrode switch is closed and a second counter 42 for counting when the electrode switch is open.

The counters start counting from a reset time provided by the controller 36 as a reset signal R and stops counting when there is a change in the electrode signal "el" also provided by the controller.

For this purpose, each counter receives at the count input a signal which is the combination (by a NAND gate) of a count signal C and either the electrode high signal or the electrode low signal.

The ring oscillator output 44 (after a further inversion by inverter 46) is provided as the clock input to the counters. The inverter 46 keeps the load on the output of the ring oscillator as low as possible, and eliminates feedback and interference from the flip-flops and counters into the ring oscillators. The inverter can be implemented as a non-inverting buffer, and it is not essential for correct functioning of the system. It may be desired for a practical circuit implementation.

Thus, during the period of time that the count signal C is high, one counter counts the ring oscillator cycles (because these control the clocking of the counter) while the electrode signal is high and the other counts the ring oscillator cycles while the electrode signal is low.

To provide a suitable period of the count signal C, a reference oscillator 47 is provided and the output is provided to the row selector 34 and to the controller 36.

The counter outputs are latched in registers 48, 50 to form the outputs OUT1 and OUT2. This latching is controlled by a store signal S generated by the controller 36.

The electrode signal el and the count signal C are generated by the controller 36.

Flip-flops 51 are used to pass the electrode switch "el" and count "C" signals eliminate potential metastability problems. These are clocked by the line 44.

The controller has a measure input Ms which is used to instruct the measurement of the array of sensor values. It also has a panic input P which is used to provide an interrupt to the measurement process, if needed.

Thus, the core of the system is an array of ring oscillator sensor circuits. All sensor circuits in one row are enabled at a time. While they are running the electrode is switched in and out of the oscillation loop. One counter counts the number of oscillator pulses with the electrode in the loop, and the other counts with the electrode out of the loop.

The time the counters are active should be exactly equal. The reference oscillator 47 is matched with the oscillators in the array, by which is meant that it has the same frequency as the oscillator in the array when there is no external capacitor connected.

The reference oscillator is used to set the counter time.

For some applications the measurement frequency has to be varied. This can easily be achieved in this system by varying the bias current of the oscillators.

The electrode must be switched with a frequency above the knee frequency of the 1/f noise. Then the two counters work as correlated double samplers and eliminate the influence of the 1/f noise. Correlated double sampling is a known technique to eliminate 1/f noise.

The thermal noise can be made arbitrarily low by choosing a sufficiently long measurement time.

Both the oscillator frequency and the knee frequency of the 1/f noise depend on the supply current. Their ratio is approximately constant: N≈fosc/fknee. The frequency will then be close to optimal for eliminating 1/f noise, without having to worry about voltage, temperature and process variations.

By way of example, a typical oscillator may run at 3 GHz with an fknee frequency of 100 MHz. In this case, the value of N would be 30.

As mentioned above, the reference oscillator is matched with the oscillators in the array. In this way, the reference oscillator frequency can be divided by N to obtain a signal to switch the electrodes in and out of the oscillators.

FIG. 2 shows a divide-by-N unit 52 for this purpose, which receives the reference oscillator signal, and generates an enable signal "en". The signal "en" is a clock gating signal (enable).

This is then used by the controller 36 to define a second clock domain, for example for deriving the electrode switch signal "el".

As there are two independent clock domains, care has to be taken that the signals that cross the domain boundaries are received correctly.

The flip-flops that pass the "el" and "count" signals eliminate potential metastability problems. The reset signal has no flip-flop as the reset signal is active much longer than two clock cycles of the oscillator, and its exact timing is not critical.

The Finite State Machine ("FSM") plus double flip-flops make sure both counters are active an exactly equal amount of time. Because of clock phase/frequency differences there will be half a clock cycle added to the wrong counter (on average). As this happens to both counters, the relative time resolution of the system is of the order of magnitude of 1/N.

The source (low) supply line connections VSS of the oscillators is through the column, not the row, to reduce the risk of interference. This also eliminates mismatch due to voltage drop along the VSS line between the VSS connections of the oscillators.

The operation of the circuit can be explained with reference to the Finite State Machine ("FSM"). The FSM runs based on the frequency of the reference oscillator, but the clock is gated every Nth cycle by the enable signal "en".

Figure 3:
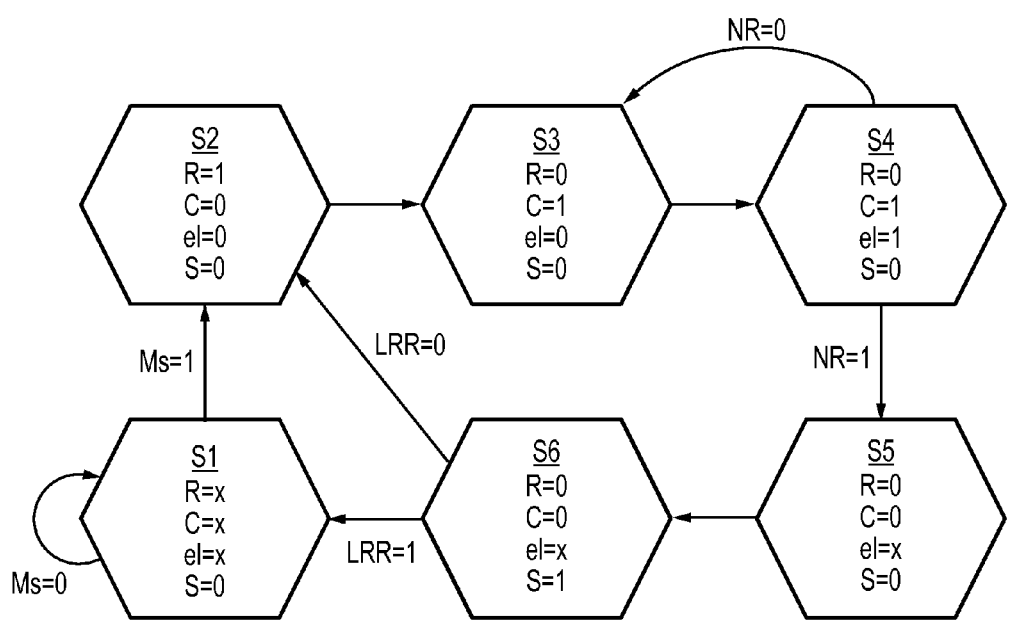
FIG. 3 is a state diagram used to explain the operation of the circuit in more detail.

FIG. 3 shows the state diagram, and shows the values of the key parameters reset (R), count (C), electrode switch (el) and store (S).

The electrode switch signal "el" is an output of the finite state machine. There is no need for the FSM to change state more often than one in every N clock cycles. By gating the clock by means of the divider 52, the dissipation is significantly reduced in a practical system.

There are six states.

State 1 is an initial/inactive state. When something goes wrong during a measurement the FSM returns to this state by pushing the panic button (so that P=1). Only the store signal S is defined as S=0 in this state to make sure that the contents of the registers keep the result of the last completed measurement. The other three parameters can take any value (i.e. set to value x, where x indicates don't care).

In response to an instruction to perform a measurement, i.e. Ms=1, the FSM moves to state 2. In this state, the row selector is reset, so that R=1. This means all oscillators in the array are disabled. The counters of the readout circuits are reset.

The FSM automatically proceeds to state 3. In state 3, the reset is lifted (so R=0). The row selector activates the oscillators in the first row of the array. The counters are released for counting (so C=1). Clock pulses are counted with the electrode disconnected (el=0). After the count (which covers a duration of N reference oscillator cycles), the FSM moves to state 4. The electrode is connected (el=1) and clock pulses are counted with the electrode connected to the oscillator.

Once the count is complete, the "Nextrow" signal is made active (NR=1) and the FSM moves to state 5.

The arrow back from state 4 to state 3 represents the repetition of these states to perform correlated double sampling.

In state 5, the counters are blocked (C=0) so the contents can be transferred to the registers 48,50.

As the data has to cross a clock domain boundary, a complete state is used for this. This takes N reference-clock cycles, which is a small overhead. If needed, this can be avoided by clocking the FSM without the clock gating.

The FSM then proceeds to state 6. The store signal is set, S=1. The counter contents are then stored in the registers. Depending on whether more rows have to be measured, the FSM goes back to the next measurement loop or returns to the initial/inactive state.

Note that the state machine moves through three states when setting up the measurement of the next row (states 5,6 and 2). This means that the division factor of the "nextrow" signal NR is M+3.

M is the number of consecutive measurements (sense capacitor selected/not selected) that are accumulated per row. At higher values of M, more measurements are accumulated, which lowers noise, at the expense of a lower frame rate (a frame being a complete sweep through all rows). A similar effect may be obtained by averaging in the signal analysis. However low values of M come with high frame rates and, therefore, high digital output data bandwidths.

Thus, the higher the value of M, the longer the measurement takes, and therefore the higher the sensitivity of the system. Typically M will be a number between 1000 and 1000000.

For this purpose, a unit 54 for division by M+3 is shown in FIG. 2, which divides the reference clock by M+3 to derive the "Nextrow" enable signal NR. The row selector thus runs at a lower frequency than the FSM.

As the counters do not count in the three set-up states, the total measurement time of one pixel is N*M clock cycles. By varying the value of N between measurement loops a "spread spectrum" can be created to reduce emissions or sensitivity to interference.

Digital systems which run at a fixed frequency can cause a lot of interference on a nearby system. Varying the frequency from time to time spreads the energy in the frequency domain and thus reduces the interference at any single frequency.

Many oscillators in a small area can give rise to injection locking. As injection completely prevents the ability of the system to measure capacitance (changes), measures can be taken to avoid injection locking if it can arise. The simplest way to do this is to make sure there is always a separation between running oscillators. This can be achieved by enabling the first, third, fifth, . . . oscillator in a row in the first measurement loop and the second, fourth, sixth, . . . oscillators in each row in the second measurement loop.

If a separation of one oscillator is not enough the rows can be divided into more sub-rows. In order not to increase the total measurement time, sub-rows of multiple rows must be activated at the same time.

The separation of active oscillators should be equal in the x and y direction in the array. For example, if the rows are divided into three sub-rows, the first sub-row of row k, the second sub-row of row k+2, and the third sub-row of row k+4 can be measured simultaneously.

In order to prevent injection locking between the reference oscillator and the oscillators in the array, the reference oscillator can be deliberately offset by a few percent. In this arrangement, the capacitance to be measured is part of the frequency-determining part of an oscillator. As time (i.e. frequency) is the quantity that can be measured most accurately, the measurement accuracy can be higher than with any other method.

Most other measurement methods convert their output signal into a time measurement, e.g. through a sigma-delta ADC. As each conversion adds noise and distortion, the measurement result cannot be better than of direct time measurement.

As measuring time only requires an accurate reference oscillator and (digital) counters, the invention provides a solution which is relatively easy to implement. It also mostly consists of digital circuits so that it is insensitive to process variations.

As one example, the invention can be applied to $CO_2$ sensors. When using a pixellated sensor, multiple $CO_2$-sensitive materials with different response characteristics can be deposited next to each other. In this way multiple responses to the same gas mixture (e.g. air+CO2+water vapor) can be obtained with essentially identical sensors. This enables the cross-sensitivities of $CO_2$-sensitive materials to water vapor to be separated. In addition, the imaging capability of a pixilated sensor array can be used to detect inhomogeneities in $CO_2$-sensitive materials deposited on the array, such as thickness variation, inclusions like air bubbles. The imaging capability can also be used to align regions of sensing materials spotted on different parts of the array in software, e.g. with the aid of pattern recognition methods. It can also be used to detect dust particles on the surface.

The invention can be used in many other applications.

For applications such capacitive imaging of living cells, pixellated sensors are inherently required.

For massively parallel sensing such as in DNA sequencing, pixellated sensors are required to achieve the highest density of sense electrode per surface area, in order to reduce cost.

By forming an array of sensor pixels (or cells), the sensor pixels can share, to a large extent, the same peripheral electronic circuits. In this way, low-frequency noise in the peripheral electronics will appear as correlated noise in the pixel signals, and therefore can be suppressed by spatial filtering methods, such as subtracting the array-averaged signal from each individual pixel signal, or similar methods, such as the correlated double/multiple sampling mentioned above.

By receiving signals from multiple individual sensor pixels, the overall sensor performance is improved. By detecting defected regions of a sensing material deposited on the array, such regions can be eliminated from further analysis. In this way, near perfect sensing materials can be constructed by signal processing.

The pixel array may for example vary from 16×16 pixels for simple applications to 1024×1024 for more demanding applications. Thus, there are typically more than 100 pixels.

In DNA sequencing, even arrays of tens of millions of sense capacitors may be used. In advanced CMOS processes like 40-nm CMOS a typical pixel may be of the order of magnitude of 2 um×2 um to 5 um×5 um, depending on the dimensions of the transistors used in the inverters, NAND gate and switches. These dimensions determine properties like the amount of 1/f noise and pixel-to-pixel variation.

The ring oscillator circuit shown uses three inverter stages (one implemented by the NAND gate). It could make use of 5 stages (or a larger odd number), without departing from the concept of the invention. Of course, more stages will hamper the possibility to integrate a large number of sensors.

The system of FIG. 2 makes use of a controller. Components that may be employed for the controller include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A capacitor sensor, comprising:
an array of sensor circuits arranged in rows and columns, each sensor circuit comprising:
  a ring oscillator having a forward path and a feedback path;
  an input for connection to a terminal of a capacitance to be measured; and
  a switch between the input and a node on a forward path or feedback path of the ring oscillator;
wherein the sensor circuit further comprises:
a measuring circuit for measuring the ring oscillator frequency of each sensor circuit with the switch open and with the switch closed, and for deriving a capacitance from a change in ring oscillator frequency, wherein the measuring circuit comprises a row selector, a measuring unit for each column and a reference oscillator;
wherein the forward path comprises exactly two inverters in series; and
wherein the node is at the input of a first of the two inverters.

2. The capacitor sensor of claim 1, wherein the switch is between the input and a node on the forward path of the ring oscillator.

3. The capacitor sensor of claim 1, further comprising a gate at the input to the forward path which controls connection of the feedback path.

4. The capacitor sensor of claim 3, wherein the forward path comprises the gate which is a NAND gate.

5. The capacitor sensor of claim 1, wherein the ring oscillator comprises an inverter after the forward and feedback paths.

6. The capacitor sensor of claim 1, wherein each measuring unit comprises a counter arrangement clocked by the ring oscillator output, for counting ring oscillator cycles during a measurement window with the switch open and with the switch closed.

7. The capacitor sensor of claim 6, wherein the counter arrangement comprises first and second counters, and wherein each counter has an output latch.

8. The capacitor sensor of claim 6, comprising a divider for dividing the reference oscillator output to derive an enable signal, wherein the controller derives the control signal for the switch from the enable signal.

9. The capacitor sensor of claim 1,
wherein the capacitor sensor is embedded in a device; and
wherein the device comprises a gas sensor, a humidity sensor, an electronic nose, an electronic tongue, a biosensor, a DNA sequencer, an imaging device for living cells, a particle detector, or a layer analysis sensor.

10. A capacitive sensing method, comprising:
for each sensor circuit of an array of sensor circuits:
  selectively coupling a terminal of a capacitance to be measured to a node in a forward path or feedback path of a respective sensor circuit ring oscillator;
  measuring the ring oscillator frequency with the terminal coupled and with the terminal decoupled;
  deriving the capacitance from a change in the ring oscillator frequency;
wherein the forward path comprises exactly two inverters in series; and
wherein the node is at the input of a first of the two inverters.

11. The method of claim 10, further comprising controlling connection of the ring oscillator feedback path thereby to implement an enable function.

12. The method of claim 10,
wherein the measuring further comprises:
selecting a row in the array of sensor circuits; and
measuring capacitances for each column in the array of sensor circuits by a counting process which is clocked by the ring oscillator output during a measurement window.

13. The method of claim 12, further comprising dividing a reference oscillator signal to determine a duration of the measurement window.

14. A capacitor sensor, comprising:
an array of sensor circuits arranged in rows and columns, each sensor circuit comprising:
  a ring oscillator having a forward path and a feedback path;
  an input for connection to a terminal of a capacitance to be measured; and
  a switch between the input and a node on a forward path or feedback path of the ring oscillator;
wherein the sensor circuit further comprises:
a measuring circuit for measuring the ring oscillator frequency of each sensor circuit with the switch open and with the switch closed, and for deriving a capacitance from a change in ring oscillator frequency, wherein the measuring circuit comprises a row selector, a measuring unit for each column and a reference oscillator;

further comprising a gate at the input to the forward path which controls connection of the feedback path;
wherein the forward path comprises the gate which is a NAND gate, and exactly two inverters in series; and
wherein the node is at the input of a first of the two inverters.

* * * * *